United States Patent
Hicks et al.

(10) Patent No.: US 6,489,512 B1
(45) Date of Patent: Dec. 3, 2002

(54) METHOD FOR MAKING ARYL HYDRAZINES AND SUBSTITUTED INDOLES

(75) Inventors: Frederick Hicks, Somerville, MA (US); Da-Ming Gou, Lexington, MA (US); Salvatore Anthony Marchese, Malden, MA (US); Lawrence J. Martel, Manchester, NH (US); Atena Necula, Everett, MA (US); Richard E. Benetti, Somerville, MA (US); Richard A. Silva, Foxboro, MA (US)

(73) Assignee: Rhodia Chirex Inc., Boston, MA (US)

( * ) Notice: Subject to any disclaimer, the term of this patent is extended or adjusted under 35 U.S.C. 154(b) by 0 days.

(21) Appl. No.: 10/177,381

(22) Filed: Jun. 21, 2002

(51) Int. Cl.[7] .............................................. C07C 251/00

(52) U.S. Cl. ....................... 564/310; 564/313; 564/314; 546/249; 546/277.4; 546/329

(58) Field of Search ................................. 564/310, 313, 564/314; 546/249, 277.4, 329

(56) References Cited

U.S. PATENT DOCUMENTS

| 3,341,538 | A | 9/1967 | Block et al. .............. 260/247.2 |
| 5,576,460 | A | 11/1996 | Buchwald et al. .......... 564/386 |
| 5,607,960 | A | 3/1997 | Wythes ....................... 514/414 |
| 5,998,438 | A | 12/1999 | Slassi et al. ................. 514/316 |
| 6,166,226 | A | 12/2000 | Buchwald et al. ........... 549/355 |
| 6,235,936 | B1 | 5/2001 | Buchwald et al. .......... 564/386 |

OTHER PUBLICATIONS

Chen et al.; Improved Fischer Indole Reaction for the Preparation of N,N–Dimethyltryptamines: Synthesis of L–695,894, a Potent 5–HT 1D Receptor Agonist; J. Org Chem. 1994, 59, 3738–3741.

Gessner et al.; "Synthesis and Dihydropteridine Reductase Inhibitory Effects of Potential Metabolites of the Neurotoxin 1–Methyl–4–phenyl–1,2,3,6–tetrahydropyridine"; J. Med. Chem. 1985, 28, 311–317.

*Primary Examiner*—Samuel Barts

(57) ABSTRACT

A method for making an indole compound includes transition metal-catalyzed arylation of a hydrazone to form an aryl hydrazone, hydrolysis of the aryl hydrazone to form an aryl hydrazine, and acid catalyzed cyclization of the aryl hydrazine to form the indole compound.

27 Claims, No Drawings

METHOD FOR MAKING ARYL HYDRAZINES AND SUBSTITUTED INDOLES

FIELD OF THE INVENTION

This invention relates to methods for making aryl hydrazines and substituted indoles, which are useful intermediates and end products in pharmaceutical and agricultural applications.

BACKGROUND OF THE INVENTION

Certain 3,5-disubstituted indole compounds have been found to be selective agonists which act on 5-hydroxytryptamine receptors and to be useful in the treatment of migrane and other medical conditions, see U.S. Pat. No. 5,607,960.

Syntheses of such indole compounds have typically been based on the approach of functionalizing an existing indole nucleus, necessitating a large number of processing steps and reduced theoretical efficiency for the sequence of steps, see for example, U.S. Pat. No. 5,998,438, which discloses synthesis of 5-(1-Aza-1-methylcyclohex-3-en-4-yl)-3-[2-(N,N-dimethylamino)ethyl]-1-H-indole. The route desclosed in the '438 patent also requires use of a toxic reagent, that is, 4-tributylstannyl-1-aza-1-tertbutoxycarbonylcyclohex-3-ene, and the use of a hazardous reagent, LAH.

There is an interest in development of a simplified synthetic route to such indole compounds.

SUMMARY OF THE INVENTION

In a first aspect, the present invention is directed to a method for making an aryl hydrazine, comprising:

(a) reacting a substrate aromatic compound, said substrate aromatic compound bearing an activated carbon atom, and a hydrazone in the presence of a transition metal catalyst under conditions suitable to form an aryl hydrazone having a new carbon-nitrogen bond between the activated carbon of the substrate aromatic compound and a nitrogen atom of the hydrazone, and (b) hydrolyzing the aryl hydrazone to form the aryl hydrazine.

The method of the present invention for making an aryl hydrazine provides a simple, two step linear synthesis of substituted aryl hydrazine compounds and does not require the use of toxic or hazardous reagents.

In a second aspect, the present invention is directed to a method for making an indole compound, comprising:

(a) reacting a substrate aromatic compound, said substrate aromatic compound bearing an activated carbon atom, and a hydrazone in the presence of a transition metal catalyst under conditions suitable to form an aryl hydrazone having a new carbon-nitrogen bond between the activated carbon of the substrate aromatic compound and a nitrogen atom of the hydrazone, (b) hydrolyzing the aryl hydrazone to form an aryl hydrazine, and (c) cyclizing the aryl hydrazine in the presence of an aldehyde or ketone and acid catalyst to form the substituted indole compound.

The method of the present invention for making an indole compound provides a simple, three step linear synthesis of substituted indole compounds and does not require the use of toxic or hazardous reagents.

DETAILED DESCRIPTION OF THE PREFERRED EMBODIMENTS

In a preferred embodiment, a substrate aromatic compound and a hydrazone are coupled to form a hydrazone according to reaction scheme 1:

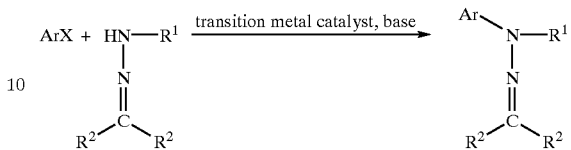

wherein:

Ar is aryl and may, optionally, be further substituted beyond X,

X is a leaving group that is capable of being replaced by a nucleophilic nitrogen in a transition metal-catalyzed arylation reaction, and $R^1$ is H, substituted or nonsubstituted alkyl, substituted or nonsubstituted alkenyl, substituted or nonsubstituted alkynyl, substituted or nonsubstituted aryl or substituted or nonsubstituted heterocyclyl, and each $R^2$ is independently H, substituted or nonsubstituted alkyl, substituted or nonsubstituted alkenyl, substituted or nonsubstituted alkynyl, substituted or nonsubstituted aryl or substituted or nonsubstituted heterocyclyl, or, alternatively, the $R^2$ groups are fused to form, together within the carbon atom to which they are each attached, a substituted or unsubstituted monocyclic cycloalkyl, cycloalkenyl, aryl or heterocyclyl ring.

As used herein, the term "substituted" denotes the conceptual replacement of a hydrogen atom of a given organic moiety with a substituent group other than a hydrogen atom and includes all permissible substituent groups, including acyclic hydrocarbon groups, alicyclic hydrocarbon groups, monocyclic aromatic hydrocarbon groups, polycyclic aromatic hydrocarbon groups, heteroacyclic groups, heterocyclic groups, fused ring systems and bridged ring systems, of which the substituents specifically described below are illustrative examples.

As used herein the term "heteroatom" means an element other than carbon, such as for example, oxygen, nitrogen and sulfur.

"Alkyl" refers to a linear, branched or cyclic saturated hydrocarbon group, preferably a ($C_1$–$C_{30}$) linear, branched or cyclic saturated hydrocarbon group that may, optionally, contain one or more heteroatoms, such as, for example, methyl, ethyl, propyl, n-butyl, isobutyl, t-butyl, neopentyl, cyclopentyl, hexyl, cyclohexyl, decyl, stearyl, eicosyl, methoxy, triacontyl, 2,5,7-trioxanonanyl, 2,5,8-triazadecenyl, and that may, optionally, be substituted at one or more positions with other moieties, such as, for example, alkyl, alkenyl, alkynyl, aryl, heterocyclyl, halo, hydroxy, sulfhydryl, hydroperoxy, carbonyl-containing groups (including, for example, carboxy, ketone, ester and aldehyde groups), alkyloxy, alkyldioxy, amino, amido, imino, hydrazino, nitro, cyanato, thiocyanato, mercapto, thiocarbonyl-containing groups (including, for example, thioketone groups, thioester groups and thioaldehyde groups), sulfonyl-containing groups (including, for example, sulfate, sulfonate and sulfamoyl groups), silyl, siloxy and phosphoruscontaining substituent groups (including, for example, phosphoranyl, phosphinyl, phosphinothioyl, phosphinimyl). Such substituent groups may themselves be further substituted with, for example, any of the groups described above as suitable substituents for alkyl groups, to form compound substituent groups, such as, for example, aralkyl, aminoalkyl, haloalkyl, heterocyclylalkyl.

"Alkenyl" refers to a linear, branched or cyclic hydrocarbon group, preferably a ($C_2$–$C_{20}$) linear, branched or cyclic hydrocarbon group, that contains one or more carbon-carbon double bonds per group and that may, optionally, contain one or more heteroatoms, such as, for example, ethenyl, propenyl, allyl, isopropenyl, ethenylidenyl, cyclopentyl, cyclohexadienyl, azanonenyl, and that may, optionally, be substituted at one or more positions with other moieties, such as, for example, any of the possible substituents described above in respect to alkyl groups.

"Alkynyl" refers to a linear, branched or cyclic unsaturated hydrocarbon group, preferably a ($C_2$–$C_{20}$) unsaturated hydrocarbon group, that contains one or more carbon-carbon triple bonds per group and that may, optionally, contain one or more heteroatoms, such as, for example, ethynyl, propynyl, thianonynyl, and that may, optionally, be substituted at one or more positions with other moieties, such as, for example, any of the possible substituents described above in respect to alkyl groups.

"Aryl" refers to an unsaturated hydrocarbon group that contains one or more six membered rings in each of which the unsaturation may be represented by three conjugated carbon-carbon double bonds, including monocyclic and polycyclic ring systems, such as, for example, phenyl, naphthyl, anthryl, phenanthryl, indenyl, fluorenyl, which may, optionally, be substituted at one or more positions with other moieties, such as, for example, any of the possible substituents described above in respect to alkyl groups.

"Heterocyclyl" refers to a saturated or unsaturated organic group that contains one or more rings in which one or more ring members is a heteroatom, preferably a nitrogen, sulfur or oxygen heteroatom, such as, for example, thiacyclopentadienyl, thiaindenyl, thianthrenyl, oxacyclopentadienyl, oxaindenyl, isobenzylfuranyl, pyranyl, azacyclopentadienyl, pyridinyl, pyrazinyl, pyrimidinyl, pyridazinyl, indolinyl, quinolinyl, isoquinolinyl, phthalazinyl, cinnolinyl, azafluorenyl, phenanthrolinyl, phenazinyl, phenothiazinyl, phenarsazinyl, isothiazolyl, isoxazolyl, phenoxazinyl, pyrrolidinyl, pyrimadinyl, imidazolidinyl, piperidinyl, piperizinyl, oxathiaanthracenyl, isoxazolyl, oxaazaanthracenyl, isothiazolyl, morpholinyl, and which may, optionally, be substituted at one or more positions with other moieties, such as, for example, any of the possible substituents described above in respect to alkyl groups.

As used herein, "halo" means fluoro, chloro, bromo or iodo, "hydroxy" means —OH, "sulfhydryl" means —SH, "hydroperoxy" means —OOH, "carbonyl" means —C(O)—, "carboxy" means —COOH, a ketone group is a group containing a carbonyl moiety that is attached to two carbon atoms, an ester group is a group containing a —C(O)OR moiety, an aldehyde group is a group containing a —CHO moiety, "alkyloxy" means —OR', "alkyldioxy" means —OOR', "amino" is conceptually a derivative of $NH_3$ in which one or more hydrogen atoms are replaced by nonacyl organic groups and includes primary, secondary and tertiary amines, "amido" includes, for example, —C(O)NR"$_2$, "imino" means =NH, "hydrazino" includes, for example, —HNNR"$_2$, "nitro" is —$NO_2$, "cyanato" is —OCN, "thiocyanato" is —SCN, "mercapto" is —SH, "thiocarbonyl" is —C(S)—, a "thioketone group" is a group containing a thiocarbonyl moiety that is attached to two carbon atoms, a "thioester group" is —C(S)OR, a "thioaldehyde" group is a group containing a —CHS moiety, "sulfonyl" is —$SO_2$—, "sulfate" includes, for example, —$OSO_2$OR", "sulfonate" includes, for example, —$O_2$SOR", "sulfamoyl" includes, for example, —$O_2$SNR"$_2$, "silyl" is —SiR"$_3$, "siloxy" is —OSiR"$_3$, "phosphino" includes —PR"$_2$, "phosphoranyl" includes, for example, —PR"$_4$, "phosphinyl" includes, for example, —P(O)R"$_2$, "phosphinothioyl" includes, for example, —P(S)R"$_2$, "phosphinimyl" includes, for example, —P(NH)R"$_2$, "aralkyl" means an alkyl group substituted with an aryl group, such as, for example, benzyl, "aminoalkyl" means an alkyl group substituted with an amino group, such as, for example, dimethylaminoethyl, "haloalkyl" means an alkyl group substituted with a halogen atom, such as, for example, chloromethyl, "heterocyclylalkyl" means an alkyl group substituted with a heterocyclyl group, such as, for example, pyrrolidinylethyl, wherein, as used above in this paragraph, R is an organic group, R' is alkyl and R" is H, alkyl or aryl.

The substrate aromatic compound ArX contains an electrophilic atom bonded to leaving group X that is susceptible to the above cross-coupling reaction. As used herein, the term "nucleophilic" refers to a chemical moiety having a reactive pair of electrons and the term "electrophilic" refers to a chemical moiety that can accept a pair of electrons from a nucleophile.

In a preferred embodiment, Ar comprises a phenyl ring that is substituted on one or more carbons of the ring, wherein each such substituent group is independently selected from substituted or nonsubstituted alkyl, substituted or nonsubstituted alkenyl, substituted or nonsubstituted alkynyl, substituted or nonsubstituted aryl or substituted or nonsubstituted heterocyclyl.

In a more highly preferred embodiment, each of the substituent groups on the phenyl ring of the Ar moiety is independently selected from alkyl, alkenyl, sulfonyl-containing groups, acyclic groups that contain one or more nitrogen heteroatoms per group and heterocyclic groups that contain one 5- or 6-membered heterocyclic ring per group, wherein the heterocyclic ring contains one or two heteroatoms, each independently selected from nitrogen, oxygen and sulfur, per ring and wherein the heterocyclic group may, optionally, be substituted on one or more atoms of the heterocyclic ring. Suitable sulfonyl-containing groups include, for example, alkylsulfate, alkylsulfonate and alkylsulfamoyl. Suitable nitrogen-containing heteroacyclic groups include, for example, cyano, thiocyano, isocyano, alkylthiocyano, alkylcyano, and —(CH2)$_n$—$NR^3R^4$, wherein n is a number from 0 to 6, and $R^3$ and $R^4$ are each independently H or ($C_1$–$C_6$)alkyl. Suitable nitrogencontaining heterocyclic groups include, for example, pyrrolyl, pyrazolyl, pyridinyl, pyrazinyl, pyrimidinyl, pyridazinyl, pyrrolidinyl, imidazolidinyl, pyrazolidinyl, pyrazolinyl, piperidinyl, piperazinyl, each of which may be substituted or nonsubstituted. Suitable oxygen-containing groups include, for example, pyranyl, furanyl, oxacyclopentyl, oxacyclohexyl, each of which may be substituted or nonsubstituted. Suitable sulfur-containing heterocyclic groups include, for example, thiophenyl, thiacyclohexyl, each of which may be substituted or nonsubstituted. Suitable hereocyclic groups containing two different heteroatoms include, for example, isothiaolyl, isooxazolyl, furazanyl, morpholinyl.

In a more highly preferred embodiment, at least one of the carbon atoms of the phenyl ring of the Ar moiety is substituted with a group selected from ($C_1$–$C_{10}$)alkyl, cyclo($C_4$–$C_6$)alkyl, ($C_2$–$C_6$)alkenyl, cyclo($C_4$–$C_{10}$) alkenyl and 5- or 6-membered heterocyclic rings that contain one nitrogen heteroatom, each of which may connected to the carbon atom of the phenyl ring via an alkylene bridging group and each of which may be nonsubstituted or substituted, for example, with one or more groups selected from hydroxy, (C₁–C₆)alkyl (C₁–C₆)alkoxy and (C₁–C₆)alkoxycarbonyl.

In a preferred embodiment, X is a halo, sulfonate or phosphonate group, more preferably halo. Preferred sulfonate groups are those according to the general formula:

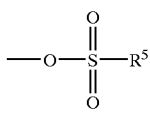

wherein $R^5$ is alkyl, aryl, fluoroalkyl, preferably trifluoromethyl, perfluoroalkyl.

Preferred phosphonate groups are those according to the general formula:

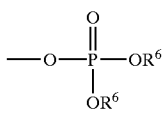

wherein each $R^6$ is independently alkyl or aryl.

The preferred halo group is chloro.

Suitable substrate aromatic compounds include, for example, 4-chloro-N-methylbenzenemethanesulfonamide, 1-bromo-3-cyclohexylbenzene, 4-(2,3-dihydropyran-2-yl)-1-trifluoromethanesulfonatobenzene,1-chloro-2-(2-pyridyl) benzene, 1-chloro-4-[2-(N,N-dimethylamino)ethyl] benzene, 4-chlorobenzonitrile, 1-bromo-4-cyanomethylbenzene,1-chloro-3-(3-hydroxy-1-butyl) benzene, 1-chloro-4-[2-(1-hydroxycyclopentyl)ethyl] benzene, 1-bromo-4-(1-hydroxybut-3-enyl)benzene and 1-methyl-4-hydroxy-(4'-chlorophenyl)-piperidine, 4-(1-azamethylcyclohex-3-en-4-yl)-1-chlorobenzene. In a highly preferred embodiment, the substrate aromatic compound is 1-methyl-4-hydroxy-(4'-chlorophenyl)-piperidine.

Suitable substrate aromatic compounds are made by known synthetic methods. The substituents on the substrate aromatic compound are selected based on structure of the desired indole product.

In a preferred embodiment, $R^1$ is H, alkyl or aryl, more preferably H.

In a preferred embodiment, each $R^2$ is independently monocyclic cycloalkyl, monocyclic cycloalkenyl or monocyclic aryl, more preferably, phenyl, or, alternatively, the $R^2$ groups are fused to form, together with the carbon atom to which they are each attached, a monocyclic 5- or 6-membered cycloalkyl, cycloalkenyl or aryl ring.

Suitable hydrazones include, for example, benzophenone hydrazone, benzaldehyde hydrazone and cyclohexanone hydrazone. In a highly preferred embodiment, the hydrazone is benzophenone hydrazone.

In a preferred embodiment, reaction of the substrate aromatic compound and the hydrazone is run with an excess of from about 4:1 to about 1.01:1, more preferably from about 2:1 to about 1.05:1, of either the substrate aromatic compound or the hydrazone. In a highly preferred embodiment the reaction of the substrate aromatic compound and the hydrazone is run with an excess of from about 1.5:1 to about 1.1:1 of the hydrazone.

In a preferred embodiment, reaction of the substrate aromatic compound and hydrazone is conducted in the presence of a transition metal catalyst and a base according to the method for transition metal-catalyzed arylation disclosed in U.S. Pat. No. 6,235,936 "METAL-CATALYZED ARYLATION OF HYDRAZINES, HYDRAZONES, AND RELATED SUBSTRATES" to Buchwald et. al., the disclosure of which is hereby incorporated herein by reference.

Suitable transition metal catalysts include, for example, soluble or insoluble complexes of platinum, palladium or nickel, more preferably palladium. Suitable palladium catalysts include, for example, $PdCl_2$, $Pd(OAc)_2$, $(CH_3CN)_2 PdCl_2$, $Pd(P(C_6H_5)_3)_4$, $Pd_2(dba)_3$ or $Pd(dba)_2$, wherein "dba" is dibenzylideneacetone, as well as supported palladium, such as palladium on carbon. In a preferred embodiment, the catalyst comprises $Pd(OAc)_2$.

In a preferred embodiment, the catalyst is provided in the reaction mixture as a metal-ligand complex wherein the transition metal catalyst is bound to a supporting ligand. In a preferred embodiment, the ligand is a monodentate alkyl or aryl phosphine or a hybrid thereof, or a chelating ligand, such as for example, alkyl and aryl derivatives of phosphines, biphosphines, amines, diamines, imines, arsines and hybrids thereof.

In a more highly preferred embodiment, the ligand is a phosphine ligand. Suitable phosphine ligands include monodentate phosphine ligands, such as, for example, trimethylphosphine, tripropylphosphine, trisobutylphosphine, tricyclohexylphosphine, trimethyl phosphite, triphenylphosphine. tri-t-butylphosphine, 2-(di-t-butyl-phosphino)biphenyl, 2-(dicyclohexylphosphino) biphenyl, 2-methyl-2'-dicyclohexylphosphinobiphenyl, 2-dimethylamino-2'-dicyclohexylphosphinobiphenyl and 2-dimethylamino-2'-di-t-butylphosphinobiphenyl, and bidentate ligands such as 2,2'-bis(diphenylphosphino)-1,1'-binaphthyl; ("BINAP"), 2,2'-bis(dicyclohexylphosphino)-1, 1'-binaphthyl, 1,2-dimethylphosphino)ethane, 1,3bis (dicyclohexylphosphino)propane. In a highly preferred embodiment, the ligand is 2-(di-t-butyl-phosphino)biphenyl.

The metal catalyst and ligand may be added to the reaction mixture as separate compounds. Alternatively, a metal ligand complex may be formed prior to addition to the reaction mixture and then added to the reaction mixture as the metal-ligand complex.

In a preferred embodiment, the coupling reaction is run in the presence of a catalytic amount of catalyst. Typically, the amount of catalyst ranges from about 0.0001 to about 20 mole %, more preferably from about 0.05 to about 5 mole %, based on the amount of limiting reactant.

In a preferred embodiment, the reaction mixture includes from about 1 to about 3 equivalents, based on the amount of hydrazone, of a base. Suitable bases include, for example, NaH, LiH, alkoxides such as sodium t-butoxide, sodium 2-methyl-2-butoxide, alkyl metal amides such as sodium amide, alkali metal bis(trialkylsilyl)amides such as lithium bis(trimethylsilyl)amide, tertiary amines such as triethylamine, 4-(dimethylamino)pyridine, alkaline earth carbonates, bicarbonates, hydroxides and phosphates, such as, for example, magnesium bicarbonate, calcium carbonate, potassium carbonate, cesium carbonate and potassium phosphate.

In a preferred embodiment, the reaction of the substrate aromatic compound and the hydrazone is conducted in a liquid reaction medium. The reaction may be run without solvent or, alternatively, may be run in a solvent that is inert under the reaction conditions. Preferably, the solvent is one in which the reaction ingredients, including the catalyst, are soluble. Suitable solvents include aliphatic or aromatic hydrocarbon solvents such as pentane, hexane, benzene, xylene and toluene, ethers such as diethyl ether and t-butyl methyl ether, tetrahydrofuran, 1,4-dioxane and 1,2-dimethoxyethane, esters such as ethylacetate, polar aprotic solvents such as acetonitrile, dimethylsulfoxide, dimethylformamide, dimethylacetamide and 1-methyl-2-pyrrolidinone, halogenated solvents such as dichloromethane, as well as mixtures of two or more solvents. In a highly preferred embodiment, the solvent is an aromatic hydrocarbon or an ether.

In general, the coupling reaction is run under mild conditions that will not adversely affect the reactants, catalyst or product. In a preferred embodiment, the coupling reaction is run at a temperature of from about 25° C. to about 300° C., more preferably from about 25° C. to about 150° C.

In a preferred embodiment, the coupling reaction is run in an inert atmosphere, such as, for example, under an argon purge or a nitrogen atmosphere.

In a preferred embodiment, the aryl hydrazone formed in the coupling step is hydrolyzed to form an aryl hydrazine salt according to reaction scheme 2.

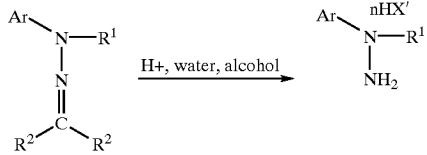

wherein

Ar, $R^1$ and $R^2$ are each defined as in scheme 1 above,

X' is halo, acetate, trifluoroacetate, sulfate or phosphate, and n is a number of from 1 to 5.

In a preferred embodiment, X' is halo.

In a preferred embodiment, the hydrolysis is run in a liquid reaction medium comprising water, an alcohol and an acid.

Suitable alcohols include, for example, methanol, ethanol isopropanol or t-butanol. In a preferred embodiment, the alcohol is methanol or ethanol.

Suitable acids include, for example, hydrochloric acid, hydrobromic acid, sulfuric acid, trifluoroacetic acid or phosphoric acid. In a preferred embodiment the acid is hydrochloric acid or sulfuric acid.

In a preferred embodiment, the hydrolysis is run in the presence of from about 2 to about 5 equivalents, based on the amount of hydrazone, of the acid.

In general, the hydrolysis is run under mild conditions that will not adversely affect the reactants or product. In a preferred embodiment, the hydrolysis is run at a temperature of from about 25° C. to about 300° C., more preferably from about 25° C. to about 150° C.

In a highly preferred embodiment, the aryl hydrazone is treated with a mixture of water, ethanol and hydrochloric acid at reflux to yield the hydrochloric acid salt of the desired hydrazine.

In a preferred embodiment, the substituted indole compound is formed by an acid catalyzed reaction of the aryl hydrazone with a ketone or an aldehyde.

In a highly preferred embodiment, the substituted indole compound formed from the aryl hydrazine via an acid-catalyzed Fischer indole cyclization reaction according to reaction scheme 3:

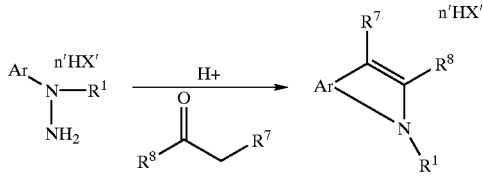

wherein:

Ar, $R^1$ and X' are each defined as in scheme 1 above, $R^7$ is substituted or nonsubstituted alkyl, substituted or nonsubstituted alkenyl, substituted or nonsubstituted aryl or substituted or nonsubstituted heterocyclyl, $R^8$ is H, substituted or nonsubstituted alkyl, substituted or nonsubstituted alkenyl, substituted or nonsubstituted aryl or substituted or nonsubstituted heterocyclyl, and n' is a number of from 1 to 5.

In a preferred embodiment, $R^7$ is substituted or nonsubstituted nitrogen-containing heteroacyclic group, more preferably a group according to $-(CH2)_n-NR^3R^4$, wherein n, $R^3$ and $R^4$ are each as described above, or a heterocyclic moiety according to:

$$-(CH_2)_m-A$$

wherein:

m is a number from 0 to 6, and

A is a nitrogen-containing heterocyclic group that contains one 5- or 6-membered heterocyclic ring per group, wherein the heterocyclic ring contains one or two nitrogen heteroatoms per ring and wherein the heterocyclic group may, optionally, be substituted on one or more atoms of the heterocyclic ring, with for example, $(C_1-C_6)$alkyl.

In a more highly preferred embodiment, $R^7$ is aminoalkyl such as aminoethyl, alkylaminoethyl such as methylaminoethyl, dialkylaminoalkyl, such as dimethylaminoethyl, pyrrolidinyl, pyrrolidinylalkyl such as pyrrolidinylethyl, alkylpyrrolidinylalkyl such as methylpyrrolidinylmethyl, pyridyl, alkylpyridyl such as methylpyridyl, piperidinyl, piperidinylalkyl such as piperidinylmethyl or alkylpiperidinylalkyl such as methylpiperidinylmethyl.

Suitable ketones include, for example, phenylacetone, cyclohexanone, ethyl pyruvate, 2-nonanone, and acetophenone.

Suitable aldehydes include, for example, 4-chlorobutyraldehyde, ethyl glyoxalate, hept-5-en-1-al, 4-piperidinylacetaldehyde, 3-cyclohexylpropionaldehyde, phenylacetaldehyde, 3-(2-N-methylpyrrolidinyl) propionaldehyde, 4-(1-pyrrolidinyl)butyraldehyde, and 4-(N,N-dimethylamino)butyraldehyde, and may be formed in situ from an aldehyde precursor, such as, for example, an acetal or bisulfite adduct. Suitable acetals include, for example, acetals such as 4-(N,N-dimethylamino) butyraldehyde diethyl acetal or 4-(N,N-dimethylamino) butyraldehyde dimethyl acetal. Suitable bisulfite adducts include, for example, 4-chloro-1-hydroxybutanesulphonic acid sodium salt.

In a preferred embodiment, dimethylaminobutyraldehyde is formed in situ from 4-(N,N-dimethylamino) butyraldehyde diethyl acetal or 4-(N,N-dimethylamino) butyraldehyde dimethyl acetal.

In a preferred embodiment, the indole synthesis reaction is run in the presence of from about 1 to about 5 equivalents, more preferably from about 1 to about 2 equivalents, aldehyde or aldehyde precursor, based on the amount of hydrazine.

Suitable acids include hydrochloric, hydrobromic acid, sulfuric acid, trifluoroacetic acid and phosphoric acid. In a preferred embodiment, the acid is sulfuric acid or phosphoric acid. In a preferred embodiment, the indole cyclization reaction is run in the presence of from about 0.5 to about 2 equivalents, more preferably from about 0.8 to about 1.2 equivalents acid, based on the amount of hydrazine.

In a preferred embodiment, the indole cyclization reaction is run in a liquid reaction medium. In a preferred embodiment, the indole synthesis reaction is conducted in a suitable solvent, such as water, alcohol or a mixture thereof.

In a preferred embodiment, the indole cyclization reaction is run under mild conditions that will not adversely affect the reactants, catalyst or product. In a preferred embodiment, the coupling reaction is run at a temperature of from about 25° C. to about 250° C., more preferably from about 25° C. to about 150° C.

The indole product may then be isolated and purified by known techniques.

In a highly preferred embodiment, a substituted aryl halide is made via a Grignard reaction and metal-catalyzed arylation of benzophenone hydrazone with the substituted aryl halide is followed by hydrolysis to give to give a substituted aryl hydrazine. The aryl hydrazine then undergoes acid-catalyzed Fischer indole synthesis to give the 5-(1-Aza-1-methylcyclohex-3-en-4-yl)-3-[2-(N,N-dimethylamino)ethyl)]-1H-indole product.

The method of the present invention is useful for making a wide variety of substituted indole compounds, such as for example, those substituted indole compounds which have been found to act on 5-HT$_1$-like receptors and to be useful in the treatment of certain medical conditions, as disclosed, for example, in U.S. Pat. No. 5,607,960, "INDOLE DERIVATIVES AS 5-HT1-LIKE AGONISTS FOR USE IN MIGRAINE" to Wythes and U.S. Pat. No. 5,998,438, "5-CYCLO INDOLE COMPOUNDS" to Slassi et. al., the respective disclosures of which are hereby incorporated herein by reference.

Exemplary substituted indole compounds include: 3-[2-N,N-dimethylamino)ethyl]-5(tetrahydropyran-2-yl)-1H-indole, 3-[2-(N,N-dimethylamino)ethyl]-5-(1-thiacyclohex-4-yl)-1H-indole, 5-(1-aza-1-tert-butoxycarbonylcyclohex-3-en-4-yl)-3-[(N-methylpyrrolidin-2-yl)methyl]-1H-indole, 5-(1-aza-1-benzylcyclohex-3-4yl)-3-(2-pyrrolidinylethyl)-1H-indole, 5-(1-aza-1-methyl-4-hydroxycyclohex-4-yl)-3 (2-pyrrolidinylethyl)-1H-indole, 5-(1-aza-1-tert-butoxycarbonyl-4-hydroxycyclohex-4-yl)-3-(2-pyrrolidinylehtyl)-1H-indole, 5-[2-hydroxycyclopentyl) ethyl]-3-[N-[2-(N,N-dimethylcarbamoyl)ethyl]-2(R)-pyrrolidinylmethyl]-1H-indole, and 5[2-(1-hydroxycyclopentyl)ethyl]-3-(2(R)-pyrrolidinylmethyl)-1H-indole.

EXAMPLE 1

5-(1-Aza-1-methylcyclohex-3-en-4-yl)-3-[2-(N,N-dimethylamino)ethyl)]-1H-indole hydrochloride was made according to reaction scheme 4, as described below.

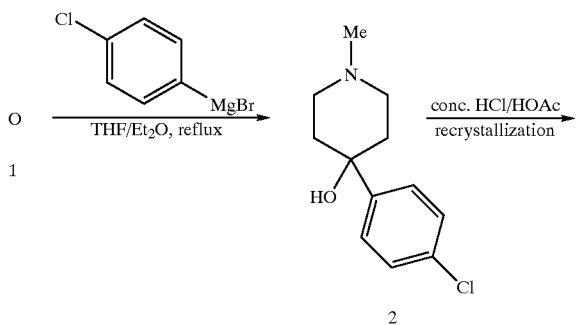

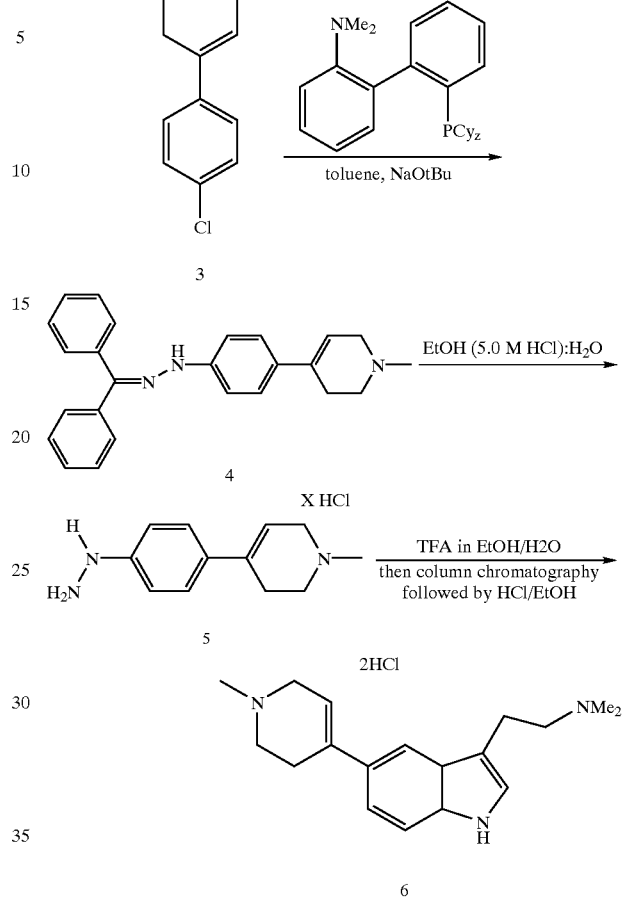

1-Methyl-4-hydroxy-(4-chlorophenyl)piperidine (2)

A dry 3-L 3 neck flask was equipped with a Claisen adapter, a mechanical stirrer, a thermocouple and a reflux condenser. The flask was charged with magnesium turnings (28 g, 1.15 mol) and THF (250 mL). A solution of 1-bromo-4-chlorobenzene (225 g, 1.18 mol) in THF (1 L) was added slowly to the stirred solution to control the exotherm (internal temperature reached 64° C.). The reaction was refluxed an additional hour and then cooled with an ice bath. A solution of 1-methyl-4-piperidone in THF (104 mL, 0.845 mol in 675 mL) was added dropwise, and the resultant reaction mixture was refluxed for 4 h. After cooling to ambient temperature, the reaction mixture was transferred to a 4 L Erlenmeyer flask and quenched with 750 mL ice water. After sitting for 12 h, the solution was transferred to a 6 L separatory funnel with 2 L methylene chloride. This produced a triphasic mixture from which the middle organic layer was collected, extracted with water (2×1 L) and brine (1 L), dried with Mg$_2$SO$_4$, and concentrated to dryness to provide 191.8 g (72%) of 1-methyl-4-hydroxy-(4-chlorophenyl)piperidine(2).

N-[4-(1-Aza-1-methylcyclohex-3-en-4-yl)-1-chlorobenzene (3)

A 3-L 3 neck flask equipped with a mechanical stirrer, a reflux condenser and a thermocouple was charged with 100 g (0.44 mol) of 2 and a 3:1 acetic acid/HCl solution (1 L).

The stirrer was engaged, and the mixture heated to reflux for 7 h. After cooling the solution to 15° C., 500 mL ice water was added followed by slow addition of KOH pellets to achieve a pH of 8 (exotherm occurred with maximum temperature of 55° C.). After stirring at ambient temperature for 60 h, the reaction mixture was transferred to a 6 L separatory funnel and extracted with dichloromethane (2 L then 1 L). The combined organic phases were washed with water (3×1 L) and brine (2×1 L), dried with $Mg_2 SO_4$, filtered and concentrated to dryness to provide 41.1 g of a tan solid. The aqueous layer was extracted again with dichloromethane (2×1 L) to provide another 12.1 g of solid. Combined yield 62.2 g (68%). 44.7 g of the crude solid were recrystallized by a literature procedure (Gessner, W. et al *J. Med. Chem.* 1985, 28, 311) to provide 41.5 g (92.8% recovery) of pure 3.

N-[4-(1-Aza-1-methylcyclohex-3-en-4-yl)phenyl benzophenone hydrazone (4)

An oven-dried, 1-L, 3necked flask was equipped with Teflon-coated magnetic stirring bar, reflux condenser, and argon inlet. The apparatus was flushed with Ar for 30 minutes. The flask was charged with 3 (10.0 g, 27.2 mmol), $Pd(OAc)_2$ (143 mg, 0.64 mmol), 2-dicyclohexylphosphino-2'-(N,N-dimethylamino)biphenyl (490 mg, 1.23 mmol), sodium tert-butoxide (9.4 g, 98 mmol), and benzophenone hydrazone (9.6 g, 49.0 mmol). The apparatus was purged for 5 more minutes with Ar and then placed under a static Ar atmosphere (balloon). Toluene (120 mL) was added via cannula and stirring initiated. The resulting mixture was placed in an 80° C. oil bath (external temperature) for 20 h. The reaction mixture was allowed to cool to ambient temperature, and the toluene was removed in vacuo. The crude product was dissolved in 200 mL acetonitrile and filtered through a pad of silica gel (150 g in a 350 mL fritted funnel). The plug was washed with 6×100 mL acetonitrile then 10×100 mL MeOH. The product containing fractions were combined and concentrated to produce a red solid, which was dissolved in hot EtOH (30 mL) and treated with hexanes (20 mL) to induce crystallization. The flask was cooled to ambient temperature and then placed in an ice bath for 1 h. The resultant solid (4) was collected by filtration and washed with cold hexanes (2×30 mL) to provide 13.75 g (76% yield).

N-[4-Aza-1-methylcyclohex-3-en-4-yl)phenyl] hydrazine hydrochloride (5)

A 250 mL pear shaped flask was equipped with a stir bar, charged with 4 (9.10 g, 24.76 mmol), and flushed with $N_2$. Water (46 mL) was added, and the flask warmed to 40° C. with vigorous stirring. After 15 minutes, 5 M ethanolic HCl (50 mL) was added via syringe, and the mixture heated to 100° C. for 25 minutes. After cooling to ambient temperature, the reaction mixture was concentrated to dryness, triturated with 4×100 mL $Et_2O$, azeotroped with toluene (2×50 mL), and dried in vacuo to produce the hydrazine hydrochloride 5 as a solid (5.56 g, 93.6% yield).

5-(1-Aza-1-methylcyclohex-3-en-4-yl)-3-[2-(N,N-dimethylamino)ethyl)]-1H-indole hydrochloride. (6)

A 200 mL round bottom flask was charged with 5.6 g (20.3 mmol) 5 and evacuated and backfilled with $N_2$. The vessel was charged with $H_2O$ (25 mL) and EtOH (12.7 mL) and stirring was initiated. Addition of 4-(N,N-dimethylamino)butyral dimethyl acetal (4.2 g, 26 mmol) was followed by slow addition of trifluoroacetic acid (8 mL). The resultant brown solution was placed in a 55° C. oil bath with stirring for 6 h and then allowed to set at ambient temperature overnight. The reaction was concentrated to dryness, and the residue dissolved in 120 mL 1 M NaOH. The aqueous solution was extracted with 2×100 mL then 3×50 mL dichloromethane. The combined dichloromethane fractions were washed with 3×125 mL $H_2O$ and concentrated to provide 5.6 g of crude material. The crude product was purified via column chromatography (250 g silica gel) eluting first with dichloromethane:MeOH (6:3.5 v/v) then dichloromethane:MeOH:triethylamine (6:3.5:0.4 v/v/v). The product collected after chromatography was treated in portions with ethanolic HCl (0.51 g product in 6 g EtOH with 1 mL 5 M ethanolic HCl; 1.6 g product in 10 g EtOH and 3 mL 5 M ethanolic HCl; 0.23 g product in 3 g EtOH with 0.5 mL 5 M ethanolic HCl). After sitting 30 min at ambient temperature, the solids were collected by filtration, washed with EtOH, and dried under vacuum. Combined yield of 5-(1-Aza-1-methylcyclohex-3-en-4-yl)-3-[2-(N,N-dimethylamino)ethyl)]1H-indole hydrochloride was 1.88 g (29% yield).

What is claimed is:

1. A method for making an aryl hydrazine, comprising:

(a) reacting a substrate aromatic compound, said substrate aromatic compound bearing an activated carbon atom, and a hydrazone in the presence of a transition metal catalyst under conditions suitable to form an aryl hydrazone having a new carbon-nitrogen bond between the activated carbon of the substrate aromatic compound and a nitrogen atom of the hydrazone, and (b) hydrolyzing the aryl hydrazone to form the aryl hydrazine.

2. The method of claim 1, wherein step (a) is conducted according to reaction scheme:

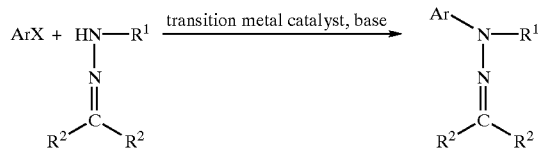

wherein:

Ar is aryl and may, optionally, be further substituted beyond X,

X is a leaving group that is capable of being replaced by a nucleophilic nitrogen in a transition metal-catalyzed arylation reaction, $R^1$ is H, substituted or nonsubstituted alkyl, substituted or nonsubstituted alkenyl, substituted or nonsubstituted alkynyl, substituted or nonsubstituted aryl or substituted or nonsubstituted heterocyclyl, and each $R^2$ is independently H, substituted or nonsubstituted alkyl, substituted or nonsubstituted alkenyl, substituted or nonsubstituted alkynyl, substituted or nonsubstituted aryl or substituted or nonsubstituted heterocyclyl, or, alternatively, the $R^2$ groups are fused to form, together within the carbon atom to which they are each attached, a substituted or unsubstituted monocyclic cycloalkyl, cycloalkenyl, aryl or heterocyclyl ring.

3. The method of claim 1, wherein step (b) is according to the reaction scheme:

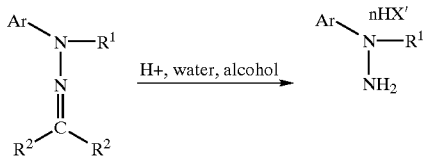

wherein

Ar is aryl, $R^1$ is H, substituted or nonsubstituted alkyl, substituted or nonsubstituted alkenyl, substituted or nonsubstituted alkynyl, substituted or nonsubstituted aryl or substituted or nonsubstituted heterocyclyl, each $R^2$ is independently H, substituted or nonsubstituted alkyl, substituted or nonsubstituted alkenyl, substituted or nonsubstituted alkynyl, substituted or nonsubstituted aryl or substituted or nonsubstituted heterocyclyl, or, alternatively, the $R^2$ groups are fused to form, together within the carbon atom to which they are each attached, substituted or unsubstituted monocyclic cycloalkyl, cycloalkenyl, aryl or heterocyclyl ring, X' is halo, acetate, trifluoroacetate, sulfate or phosphate, and n is a number of from 1 to 5.

4. The method of claim 3, wherein the alcohol comprises one or more of methanol, ethanol, isopropanol and t-butanol.

5. The method of claim 3, wherein the H+ is derived from or more of hydrochloric acid, hydrobromic acid, sulfuric acid, trifluoroacetic acid and phosphoric acid.

6. A method for making an indole compound, comprising:

(a) reacting a substrate aromatic compound, said substrate aromatic compound bearing an activated carbon atom, and a hydrazone in the presence of a transition metal catalyst under conditions suitable to form an aryl hydrazone having a new carbon-nitrogen bond between the activated carbon of the substrate aromatic compound and a nitrogen atom of the hydrazone, (b) hydrolyzing the aryl hydrazone to form an aryl hydrazine, and (c) cyclizing the aryl hydrazine in the presence of an acid catalyst to form the substituted indole compound.

7. The method of claim 6, wherein the substrate aromatic compound is according to the formula ArX, wherein Ar is aryl and may, optionally, be further substituted beyond X, and X is a leaving group that is capable of being replaced by a nucleophilic nitrogen in a transition metal-catalyzed arylation reaction.

8. The method of claim 7, wherein Ar comprises a phenyl ring that is substituted on one or more carbons of the ring, wherein each such substituent group is independently selected from substituted or nonsubstituted alkyl, substituted or nonsubstituted alkenyl, substituted or nonsubstituted alkynyl, substituted or nonsubstituted aryl or substituted or nonsubstituted heterocyclyl.

9. The method of claim 8, wherein at least one of the carbon atoms of the phenyl ring of the Ar moiety is substituted with a group selected from $(C_1-C_{10})$alkyl, cyclo$(C_4-C_6)$alkyl, $(C_2-C_6)$alkenyl, cyclo$(C_4-C_{10})$alkenyl and 5- or 6-membered heterocyclic rings that contain one nitrogen heteroatom, each of which may connected to the carbon atom of the phenyl ring via an alkylene bridging group and each of which may be nonsubstituted or substituted, for example, with one or more groups selected from hydroxy, $(C_1-C_6)$alkyl $(C_1-C_6)$alkoxy and $(C_1-C_6)$alkoxycarbonyl.

10. The method of claim 6, wherein the hydrazone is according to the formula $R^1HN-N=CR^2_2$, wherein $R^1$ is H, substituted or nonsubstituted alkyl, substituted or nonsubstituted alkenyl, substituted or nonsubstituted alkynyl, substituted or nonsubstituted aryl or substituted or nonsubstituted heterocyclyl, and each $R^2$ is independently H, substituted or nonsubstituted alkyl, substituted or nonsubstituted alkenyl, substituted or nonsubstituted alkynyl, substituted or nonsubstituted aryl or substituted or nonsubstituted heterocyclyl, or, alternatively, the $R^2$ groups are fused to form, together within the carbon atom to which they are each attached, a substituted or unsubstituted monocyclic alkyl, aryl or heterocyclyl ring.

11. The method of claim 10, wherein $R^1$ is H, alkyl or aryl and each $R^2$ is independently monocyclic cycloalkyl, monocyclic cycloalkenyl or monocyclic aryl or the $R^2$ groups are fused to form, together with the carbon atom to which they are each attached, a monocyclic 5- or 6-membered cycloalkyl, cycloalkenyl or aryl ring.

12. The method of claim 6, wherein reaction of the substrate aromatic compound and hydrazone is conducted in the presence of a transition metal catalyst and a base.

13. The method of claim 6, wherein step (a) is conducted according to reaction scheme:

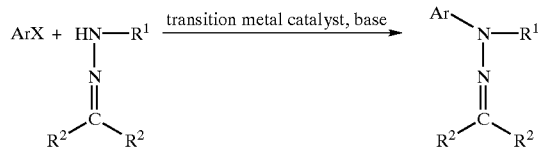

wherein:

Ar is aryl and may, optionally, be further substituted beyond X,

X is a leaving group that is capable of being replaced by a nucleophilic nitrogen in a transition metal-catalyzed arylation reaction, $R^1$ is H, substituted or nonsubstituted alkyl, substituted or nonsubstituted alkenyl, substituted or nonsubstituted alkynyl, substituted or nonsubstituted aryl or substituted or nonsubstituted heterocyclyl, and $R^2$ is independently H, substituted or nonsubstituted alkyl, substituted or nonsubstituted alkenyl, substituted or nonsubstituted alkynyl, substituted or nonsubstituted aryl or substituted or nonsubstituted heterocyclyl, or, alternatively, the $R^2$ groups are fused to form, together within the carbon atom to which they are each attached, substituted or unsubstituted monocyclic cycloalkyl, cycloalkenyl, aryl or heterocyclyl ring.

14. The method of claim 6, wherein the aryl hydrazone is according to the formula $R^1ArN-N=CR^2_2$, wherein Ar is aryl and $R^1$ and each $R^2$ are each independently H, substituted or nonsubstituted alkyl, substituted or nonsubstituted alkenyl, substituted or nonsubstituted alkynyl, substituted or nonsubstituted aryl or substituted or nonsubstituted heterocyclyl.

15. The method of claim 6, wherein the hydrolysis is run in a liquid reaction medium comprising water, an alcohol and an acid.

16. The method of claim 15, wherein the alcohol comprises one or more of methanol, ethanol, isopropanol and t-butanol.

17. The method of claim 15, wherein the acid comprises on or more of hydrochloric acid, hydrobromic acid, sulfuric acid, trifluoroacetic acid and phosphoric acid.

18. The method of claim 15, wherein the aryl hydrazone is treated with a mixture of water, ethanol and hydrochloric acid at reflux to yield a hydrochloric acid salt of the hydrazine.

19. The method of claim 6, wherein step (b) is according to the reaction scheme:

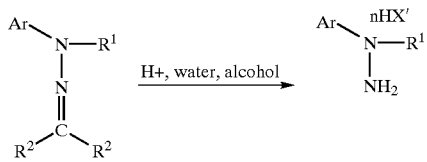

wherein
Ar is aryl,
R$^1$ is H, substituted or nonsubstituted alkyl, substituted or nonsubstituted alkenyl, substituted or nonsubstituted alkynyl, substituted or nonsubstituted aryl or substituted or nonsubstituted heterocyclyl,
each R$^2$ is independently H, substituted or nonsubstituted alkyl, substituted or nonsubstituted alkenyl, substituted or nonsubstituted alkynyl, substituted or nonsubstituted aryl or substituted or nonsubstituted heterocyclyl, or, alternatively, the R$^2$ groups are fused to form, together within the carbon atom to which they are each attached, substituted or unsubstituted monocyclic cycloalkyl, cycloalkenyl, aryl or heterocyclyl ring,
X' is halo, acetate, trifluoroacetate, sulfate or phosphate, and
n is a number of from 1 to 5.

20. The method of claim 6, wherein the aryl hydrazine is cyclized by an acid-catalyzed reaction of the aryl hydrazine with a ketone or an aldehyde.

21. The method of claim 20, wherein the aldehyde is formed in situ from an acetal or a bisulfite adduct.

22. The method of claim 6, wherein the ketone or aldehyde is according to the structural formula:

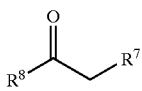

wherein:
R$^7$ is substituted or nonsubstituted alkyl, substituted or nonsubstituted alkenyl, substituted or nonsubstituted aryl or substituted or nonsubstituted heterocyclyl,
R$^8$ is H, substituted or nonsubstituted alkyl, substituted or nonsubstituted alkenyl, substituted or nonsubstituted aryl or substituted or nonsubstituted heterocyclyl.

23. The method of claim 22, wherein R$^7$ is a nitrogen-containing heteroacyclic group, according to the formula —(CH2)$_n$—NR$^3$R$^4$, or a heterocyclic moiety according to:

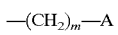

wherein R$^3$ and R$^4$ are each independently H or (C$_1$–C$_6$) alkyl, and A is a nitrogen-containing heterocyclic group that contains one 5- or 6-membered heterocyclic ring per group, wherein the heterocyclic ring contains one or two nitrogen heteroatoms per ring and wherein the heterocyclic group may, optionally, be substituted on one or more atoms of the heterocyclic ring.

24. The method of claim 22, wherein R$^8$ is H.

25. The method of claim 6, wherein the substituted indole is isolated in the form of a salt according to the formula:

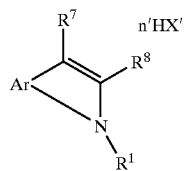

wherein
Ar is aryl,
R$^1$ is H, substituted or nonsubstituted alkyl, substituted or nonsubstituted alkenyl, substituted or nonsubstituted alkynyl, substituted or nonsubstituted aryl or substituted or nonsubstituted heterocyclyl,
R$^7$ is substituted or nonsubstituted alkyl, substituted or nonsubstituted alkenyl, substituted or nonsubstituted aryl or substituted or nonsubstituted heterocyclyl,
R$^8$ is H, substituted or nonsubstituted alkyl, substituted or nonsubstituted alkenyl, substituted or nonsubstituted aryl or substituted or nonsubstituted heterocyclyl, and
X' is halo, acetate, trifluoroacetate, sulfate or phosphate.

26. The method off claim 6, wherein step (c) is conducted according to the reaction scheme:

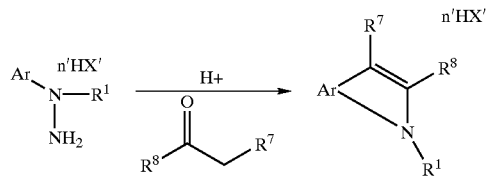

wherein:
Ar is aryl,
R$^1$ is H, substituted or nonsubstituted alkyl, substituted or nonsubstituted alkenyl, substituted or nonsubstituted alkynyl, substituted or nonsubstituted aryl or substituted or nonsubstituted heterocyclyl,
R$^7$ is substituted or nonsubstituted alkyl, substituted or nonsubstituted alkenyl, substituted or nonsubstituted aryl or substituted or nonsubstituted heterocyclyl,
R$^8$ is H, substituted or nonsubstituted alkyl, substituted or nonsubstituted alkenyl, substituted or nonsubstituted aryl or substituted or nonsubstituted heterocyclyl,
X' is halo, acetate, trifluoroacetate, sulfate or phosphate, and
n' is a number of from 1 to 5.

27. A method for making an indole compound, comprising:
(a) reacting a substrate aromatic compound and a hydrazone to form an aryl hydrazone according to reaction scheme:

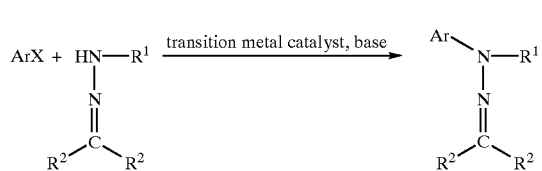

wherein:
Ar is aryl and may, optionally, be further substituted beyond X,
X is a leaving group that is capable of being replaced by a nucleophilic nitrogen in a transition metal-catalyzed arylation reaction, R[1] is H, substituted or nonsubstituted alkyl, substituted or nonsubstituted alkenyl, substituted or nonsubstituted alkynyl, substituted or nonsubstituted aryl or substituted or nonsubstituted heterocyclyl, and each R[2] is independently H, substituted or nonsubstituted alkyl, substituted or nonsubstituted alkenyl, substituted or nonsubstituted alkynyl, substituted or nonsubstituted aryl or substituted or nonsubstituted heterocyclyl, or, alternatively, the R[2] groups are fused to form, together within the carbon atom to which they are each attached, a substituted or unsubstituted monocyclic alkyl, aryl or heterocyclyl ring, (b) hydrolyzing the aryl hydrazone to form an aryl hydrazine according to the reaction scheme:

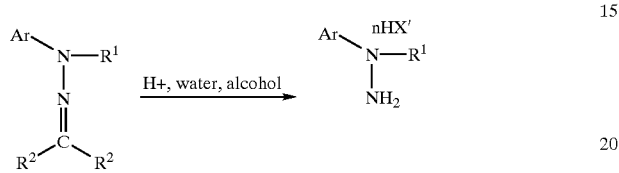

wherein
Ar R[1] and R[2] are each defined as above,
X' is halo, acetate, trifluoroacetate, sulfate or phosphate, and
n is a number of from 1 to 5, and (c) cyclizing the aryl hydrazine with an aldehyde in the presence of an acid catalyst to form the substituted indole compound, according to the reaction scheme:

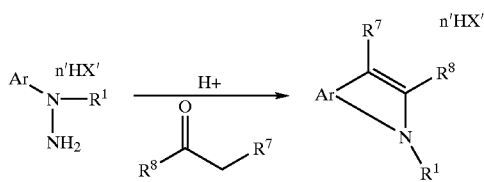

wherein:
Ar, R[1] and X' are each defined as above,
R[7] is substituted or nonsubstituted alkyl, substituted or nonsubstituted alkenyl, substituted or nonsubstituted aryl or substituted or nonsubstituted heterocyclyl,
R[8] is H, substituted or nonsubstituted alkyl, substituted or nonsubstituted alkenyl, substituted or nonsubstituted aryl or substituted or nonsubstituted heterocyclyl, and
n' is a number of from 1 to 5.

* * * * *